US010828001B2

(12) United States Patent
Yoshida

(10) Patent No.: US 10,828,001 B2
(45) Date of Patent: Nov. 10, 2020

(54) X-RAY IMAGING APPARATUS

(71) Applicant: Shimadzu Corporation, Kyoto (JP)

(72) Inventor: Takanori Yoshida, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/285,506

(22) Filed: Feb. 26, 2019

(65) Prior Publication Data

US 2019/0261939 A1    Aug. 29, 2019

(30) Foreign Application Priority Data

Feb. 26, 2018   (JP) .................................. 2018-032071

(51) Int. Cl.
| | | |
|---|---|---|
| *G01N 23/04* | (2018.01) | |
| *A61B 6/00* | (2006.01) | |
| *A61B 6/04* | (2006.01) | |

(52) U.S. Cl.
CPC .......... *A61B 6/5241* (2013.01); *A61B 6/0407* (2013.01); *A61B 6/0487* (2020.08); *A61B 6/463* (2013.01); *A61B 6/504* (2013.01); *A61B 6/547* (2013.01); *A61B 6/584* (2013.01)

(58) Field of Classification Search
CPC ..... A61B 6/5241; A61B 6/0457; A61B 6/463; A61B 6/504; A61B 6/584; A61B 6/0407; A61B 6/00; A61B 6/547
See application file for complete search history.

(56) References Cited

U.S. PATENT DOCUMENTS

| | | | | |
|---|---|---|---|---|
| 9,326,702 B2* | 5/2016 | Eichler | ................. | A61B 6/102 |
| 9,877,693 B2 | 1/2018 | Toyoda et al. | | |
| 10,157,491 B2* | 12/2018 | Florent | ................ | A61B 8/5261 |
| 2004/0101103 A1* | 5/2004 | Warp | ................... | A61B 6/4233 |
| | | | | 378/98.12 |
| 2004/0247081 A1* | 12/2004 | Halsmer | ................. | A61B 6/00 |
| | | | | 378/108 |
| 2006/0034421 A1* | 2/2006 | Barkow | .................. | A61B 6/04 |
| | | | | 378/20 |
| 2008/0114238 A1* | 5/2008 | Lloyd | ................. | A61B 6/4405 |
| | | | | 600/436 |
| 2008/0119725 A1* | 5/2008 | Lloyd | ................... | A61B 90/36 |
| | | | | 600/424 |
| 2010/0183116 A1* | 7/2010 | Zaiki | .................... | A61B 6/464 |
| | | | | 378/8 |
| 2015/0047125 A1* | 2/2015 | Bae | ..................... | A61B 6/0407 |
| | | | | 5/601 |

(Continued)

FOREIGN PATENT DOCUMENTS

| | | | |
|---|---|---|---|
| JP | 2011015912 A | * | 1/2011 |
| JP | 5085204 B2 | | 11/2012 |

(Continued)

OTHER PUBLICATIONS

Philips Product Catalogue, Image guided therapy. p. 9: "Preparing your next run without fluoroscopy," Feb. 2017.

*Primary Examiner* — Kiho Kim
(74) *Attorney, Agent, or Firm* — Muir Patent Law, PLLC

(57) ABSTRACT

In an X-ray imaging apparatus, an image processor concurrently displays, on an image display, a long image in which a frame indicating an imaging range of an imager is displayed and an X-ray image or a processed image containing position information that overlaps at least with position information of the frame.

20 Claims, 14 Drawing Sheets

(56) References Cited

U.S. PATENT DOCUMENTS

| | | | |
|---|---|---|---|
| 2015/0250441 A1* | 9/2015 | Okuno | A61B 6/06 |
| | | | 378/62 |
| 2016/0220214 A1* | 8/2016 | Yamada | A61B 6/52 |
| 2016/0278732 A1* | 9/2016 | Amiri | A61B 6/4405 |
| 2017/0265826 A1* | 9/2017 | Ancar | A61B 6/465 |
| 2018/0214103 A1 | 8/2018 | Okubo | |
| 2019/0261939 A1* | 8/2019 | Yoshida | A61B 6/463 |

FOREIGN PATENT DOCUMENTS

| | | | |
|---|---|---|---|
| JP | 2015112298 A * | 6/2015 | |
| JP | 2018-121745 A | 8/2018 | |
| WO | 2015/045005 A1 | 4/2015 | |

* cited by examiner

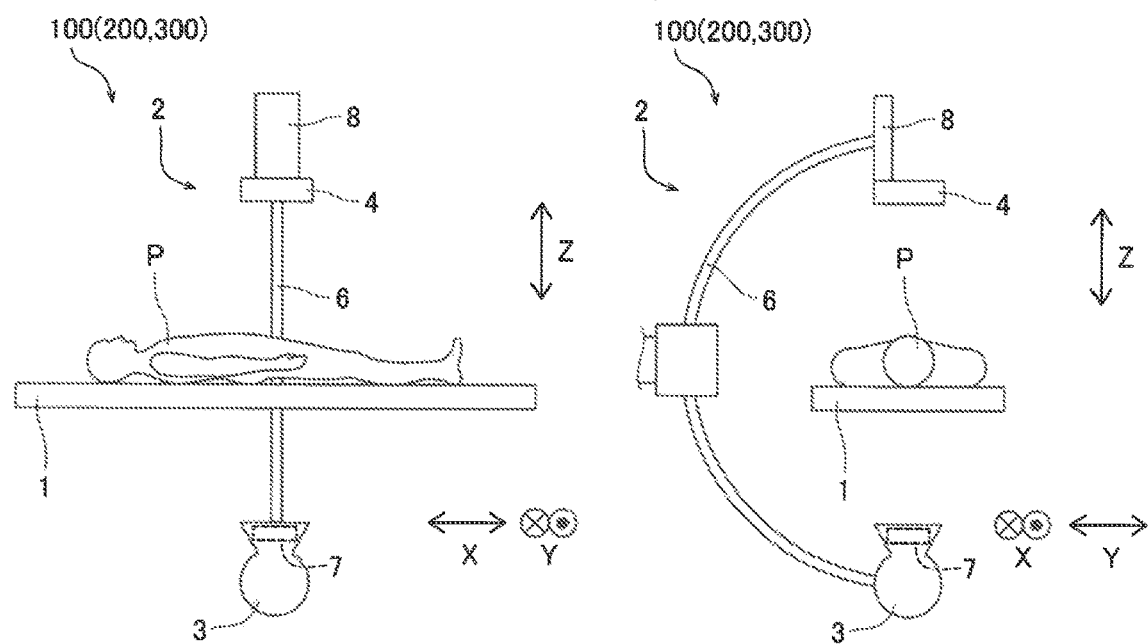
FIG.1A
FIG.1B
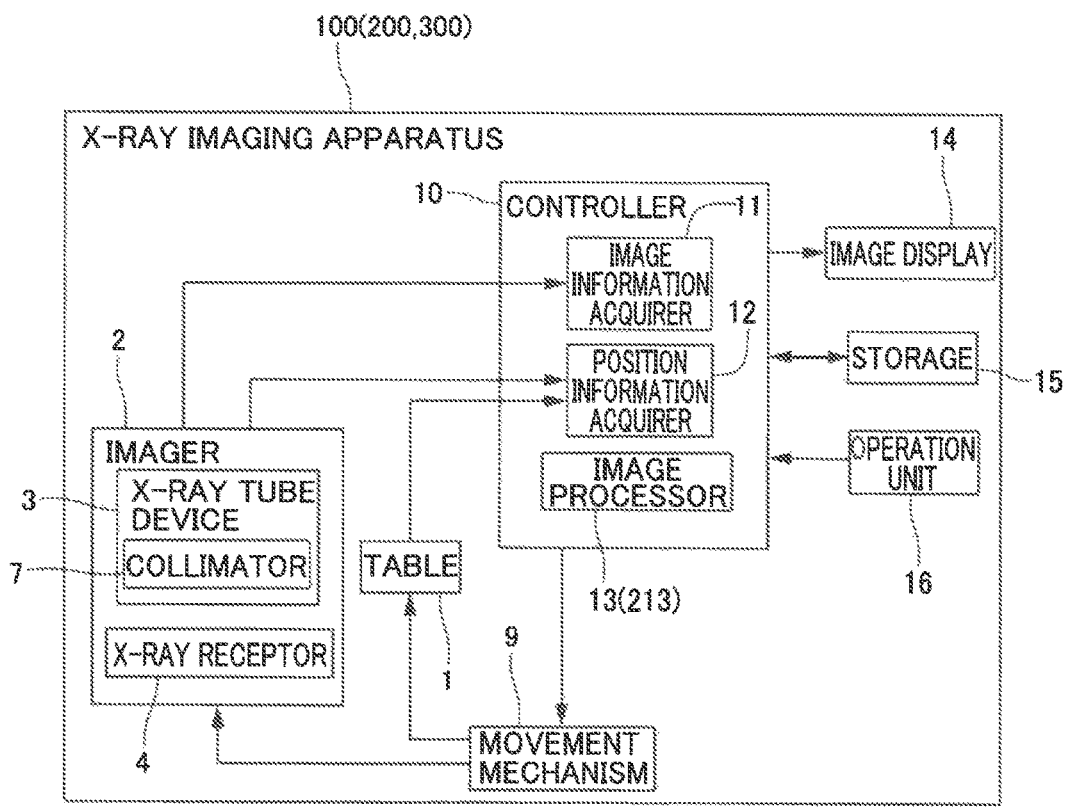
FIG.2

FIG.3A  TABLE MOVEMENT IMAGING
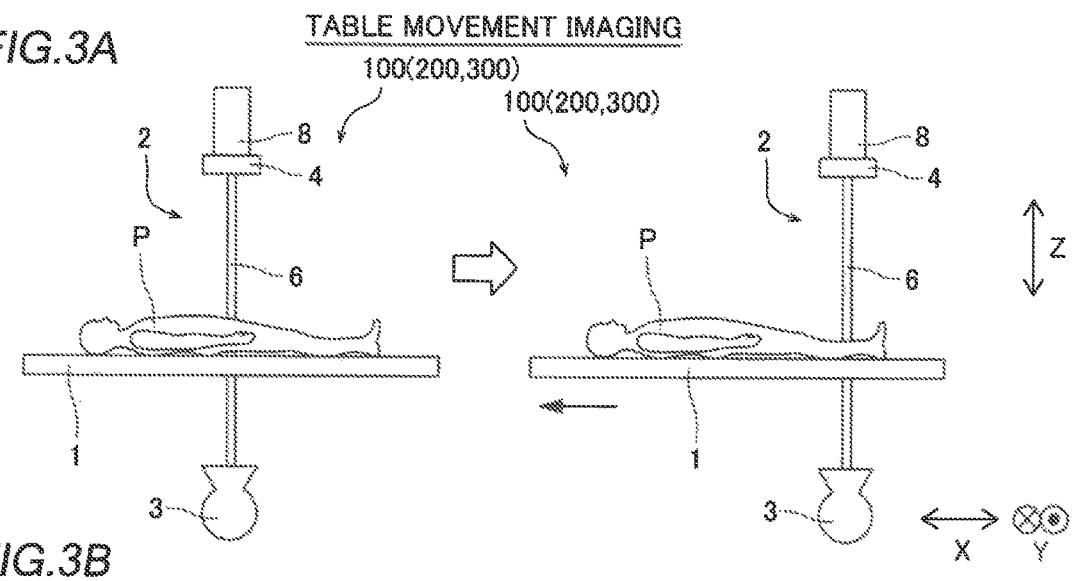
FIG.3B
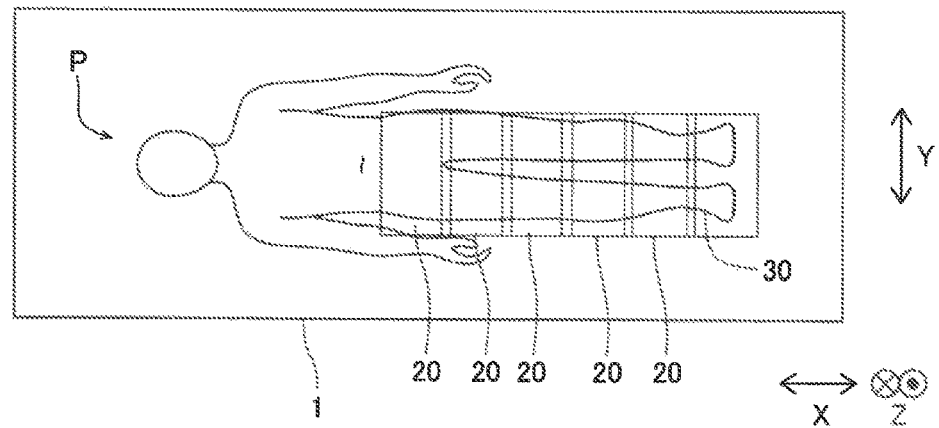
FIG.4  GENERATION OF LONG IMAGE
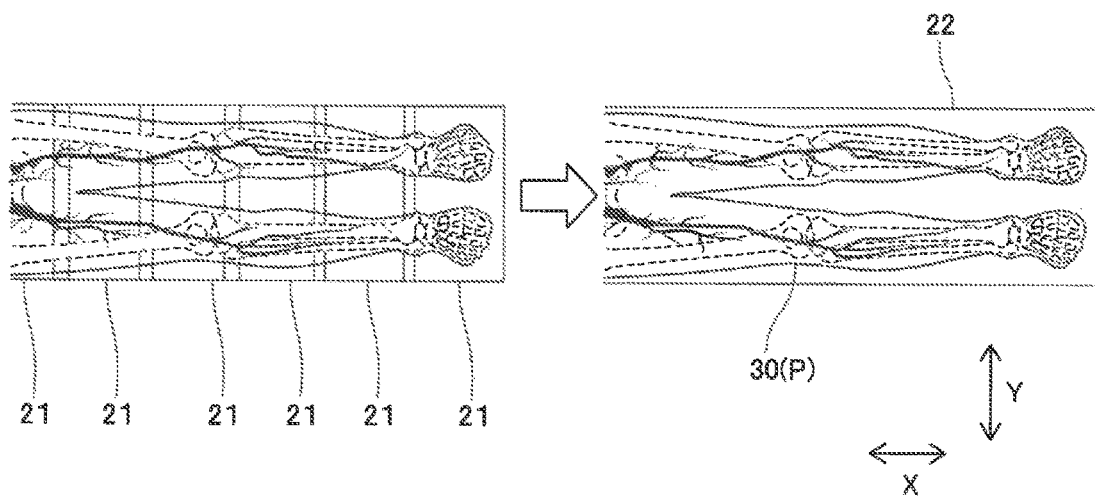

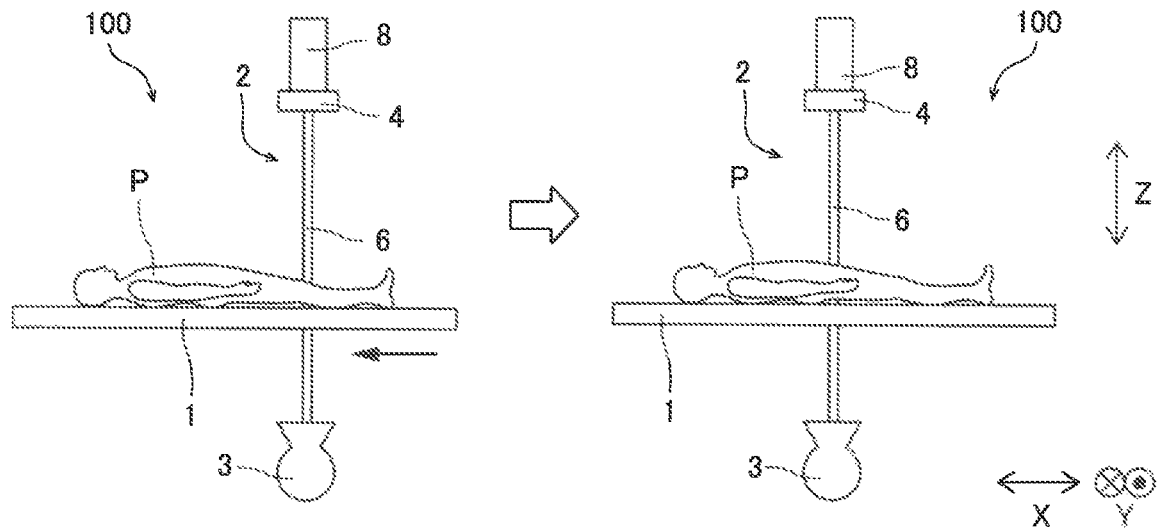

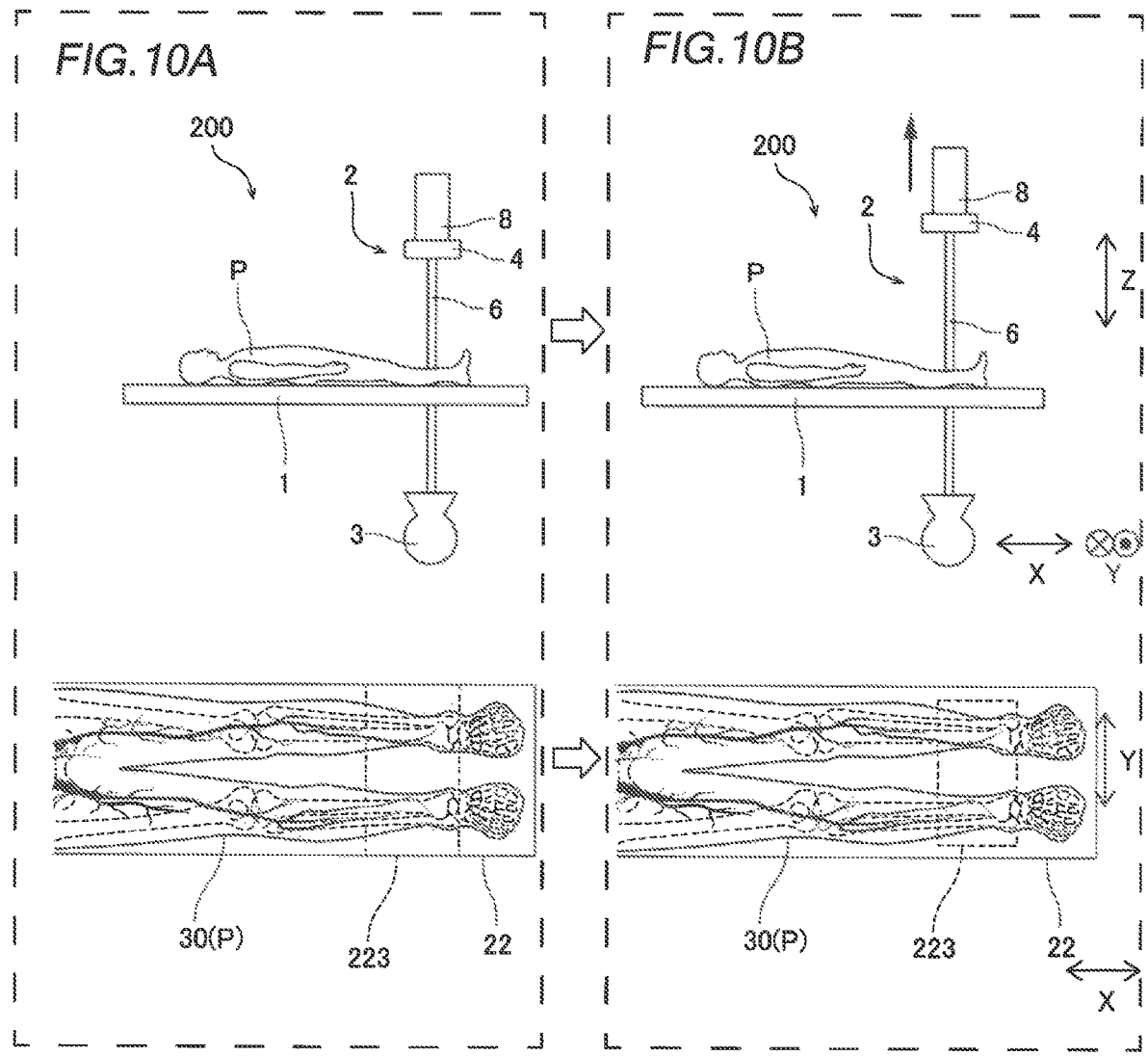

FIG.11A
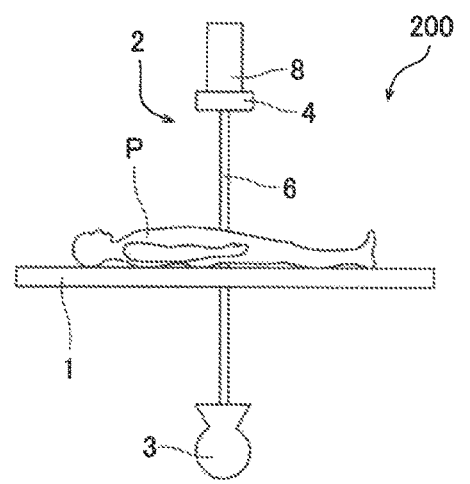
FIG.11B
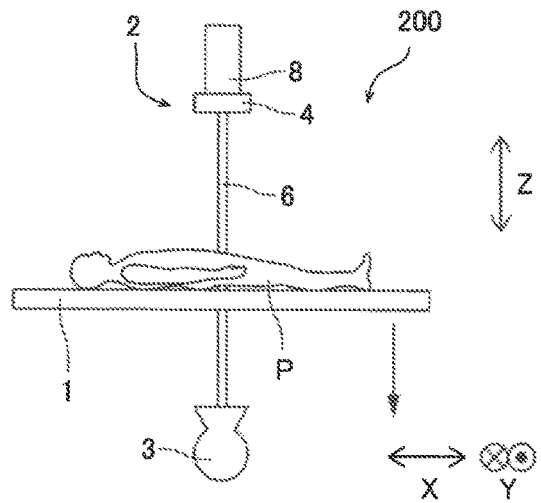
FIG.12A
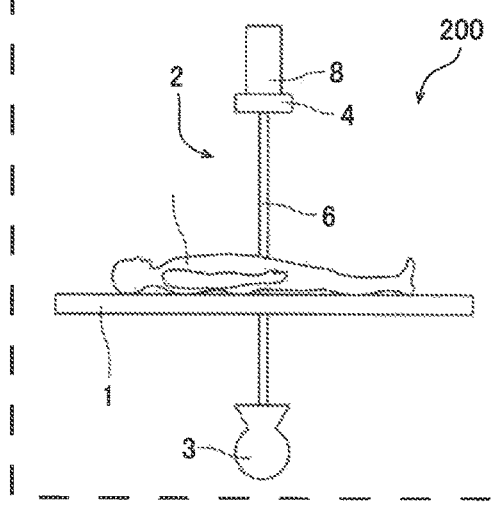
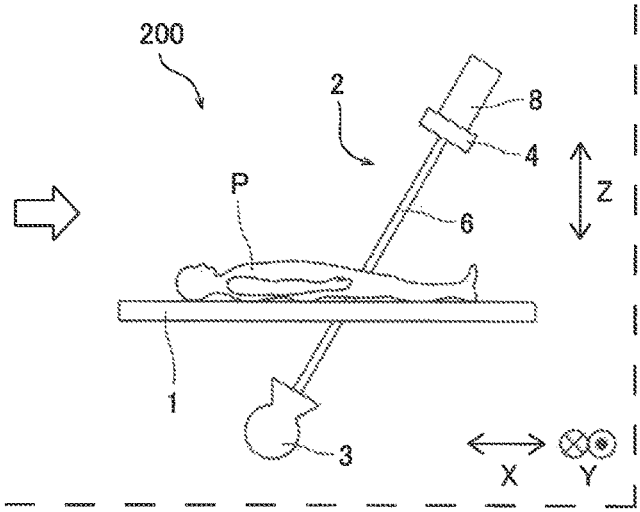
FIG.12B
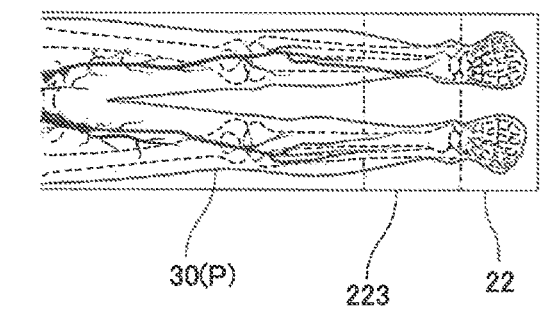
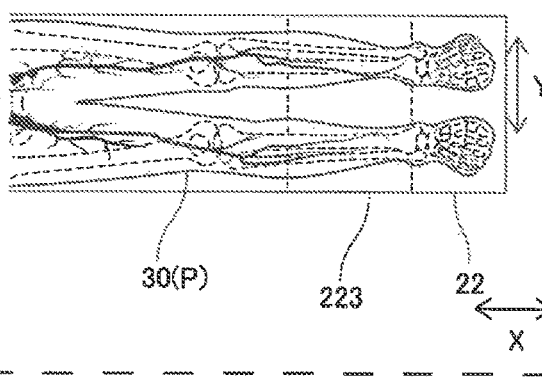

X-RAY IMAGING APPARATUS

CROSS-REFERENCE TO RELATED APPLICATIONS

This application claims the benefit of priority to Japanese Patent Application No. 2018-032071 filed on Feb. 26, 2018. The entire contents of this application are hereby incorporated herein by reference.

BACKGROUND OF THE INVENTION

Field of the Invention

The present invention relates to an X-ray imaging apparatus.

Description of the Background Art

An X-ray imaging apparatus that detects X-rays that have passed through a subject and images the inside of the subject is known in general, as disclosed in Japanese Patent No. 5085204, for example.

Japanese Patent No. 5085204 discloses an X-ray imaging apparatus including a bed that supports a subject, a radiation generator that irradiates the subject with radiation, a radiation detector that faces the radiation generator and detects radiation transmitted through the subject, an image generator that generates a fluoroscopic image based on the radiation detected by the radiation detector, and a bed driving mechanism. In the X-ray imaging apparatus disclosed in Japanese Patent No. 5085204, the bed driving mechanism is controlled to move the bed such that the radiation generator and the radiation detector are moved in the longitudinal direction of the subject. While the bed is moving, radiation is sequentially applied to the subject from the radiation generator, the radiation transmitted through the subject is detected each time by the radiation detector, and a radiographic image is captured as a fluoroscopic image (table movement imaging is performed).

An X-ray imaging apparatus such as that disclosed in Japanese Patent No. 5085204 can generate an image (long image) longer than one X-ray image by joining X-ray images acquired by "table movement imaging" based on positional information at the time of capturing the respective X-ray images. Therefore, the X-ray imaging apparatus disclosed in Japanese Patent No. 5085204 is used when a region to be diagnosed cannot fit into one X-ray image as in the case in which the lower limb is imaged.

However, in the X-ray imaging apparatus disclosed in Japanese Patent No. 5085204, X-ray images in which misalignment has occurred are generated when the subject moves at the time of capturing the original X-ray images from which the long image is generated, and thus misalignment occurs on the joined long image. Therefore, there is a problem that the accurate position and shape of a target portion may not be grasped when treatment or diagnosis is performed based on the long image in which misalignment has occurred.

SUMMARY OF THE INVENTION

The present invention has been proposed in order to solve the aforementioned problem, and an object of the present invention is to provide an X-ray imaging apparatus that enables a user to grasp the accurate position and shape of a target portion of a long image.

In order to attain the aforementioned object, an X-ray imaging apparatus according to an aspect of the present invention includes a table on which a subject is placed, an imager that irradiates the subject with X-rays, detects the X-rays transmitted through the subject, and captures a plurality of X-ray images, a movement mechanism that changes a relative position of the table to the imager, a position information acquirer that acquires position information about the relative position of the table to the imager, an image processor that joins the plurality of X-ray images captured with a change in the relative position by the movement mechanism based on the position information acquired by the position information acquirer to generate a long image, and an image display that displays an X-ray image of the plurality of X-ray images or a processed image obtained by performing image processing on the X-ray image and the long image. The image processor concurrently displays, on the image display, the long image in which a frame indicating an imaging range of the imager is displayed and the X-ray image or the processed image containing position information that overlaps at least with position information of a portion of the long image in which the frame is displayed.

As described above, the X-ray imaging apparatus according to this aspect of the present invention concurrently displays, on the image display, the X-ray image or the processed image containing the position information that overlaps at least with the position information of the portion in which the frame is displayed when displaying the frame indicating the imaging range of the imager. Accordingly, misalignment that has occurred in the long image can be compensated by visually checking the X-ray image or the processed image concurrently displayed on the image display, and thus the accurate position and shape of a target portion can be grasped. Furthermore, the X-ray image or the processed image that enables a user to accurately grasp the target portion is displayed on the image display, and the frame indicating the imaging range of the imager is displayed in the long image such that the user can accurately grasp a portion to be imaged without performing additional X-ray irradiation to the subject.

In the aforementioned X-ray imaging apparatus according to this aspect, the image processor preferably sequentially changes the X-ray image or the processed image to be displayed concurrently with the long image on the image display, based on movement of the frame displayed in the long image. According to this structure, the X-ray image or the processed image to be displayed concurrently with the long image is sequentially switched based on the movement of the frame displayed in the long image, and thus the user can continue to grasp the accurate position and shape of each target portion according to the movement of the frame.

In this case, the position information acquirer preferably acquires the position information of the portion of the long image in which the frame is displayed after the movement, and the image processor preferably sequentially changes the X-ray image or the processed image to be displayed concurrently with the long image on the image display, based on the position information of the portion of the long image in which the frame is displayed after the movement acquired by the position information acquirer. According to this structure, when the frame is moved, the X-ray image or the processed image containing the position information that overlaps at least with the position information of the portion of the long image in which the frame is displayed after the movement is constantly displayed on the image display based on the position information of the portion of the long image in which the frame is displayed after the movement. Consequently, the X-ray image or the processed image containing the position information corresponding to the frame displayed in the long image can be more accurately and reliably displayed on the image display.

In the aforementioned structure in which the X-ray image or the processed image to be displayed is sequentially changed based on the position information of the portion of the long image in which the frame is displayed after the movement, the image processor preferably sequentially changes the X-ray image or the processed image to be displayed concurrently with the long image on the image display, based on the position information of the portion of the long image in which the frame is displayed after the movement and a predetermined condition. According to this structure, the X-ray image or the processed image in accordance with the predetermined condition in addition to the position information can be displayed. Consequently, a more preferable X-ray image or processed image used for treatment or diagnosis can be displayed on the image display by appropriate setting of a condition such as setting, by the user, of a condition for selecting an image that enables the user to grasp the accurate position and shape of the target portion from among the plurality of X-ray images obtained by imaging the same portion.

In the aforementioned X-ray imaging apparatus according to this aspect, the movement mechanism preferably changes the relative position of the table to the imager based on movement of the frame displayed in the long image by a user's operation. According to this structure, when the frame is moved by the user's operation, the relative position of the table to the imager is automatically changed, and thus the user does not need to move the table, and can more easily perform a step from treatment or diagnosis to imaging for the next treatment or diagnosis. In addition, when the frame is moved by the user's operation, the relative position of the table to the imager is automatically changed, and thus the imager can be moved to the target portion without additional X-ray irradiation.

In the aforementioned X-ray imaging apparatus according to this aspect, the frame preferably indicates a current imaging range of the imager based on the position information, and the image processor preferably moves the frame displayed in the long image based on the change in the relative position of the table to the imager by the movement mechanism. According to this structure, when the relative position of the table to the imager is changed, the frame displayed in the long image is automatically moved to a portion corresponding to the imaging range of the imager after the change, and thus it is not necessary for the user to perform an operation of moving the frame in the long image. In addition, when changing the relative positions of the imager and the table so as to obtain a desired imaging position, the user can perform it while checking the frame in the long image and the X-ray image or the processed image, and thus positioning can be performed more easily.

In this case, the image processor preferably adjusts a shape or size of the frame displayed in the long image based on a change in the position information due to a change in a position of the imager, the change in the position information due to a change in a height position of the table, the change in the position information due to a change in an angle between the table and the imager, or a change in an X-ray field of the imager. According to this structure, the frame that reflects the change in the height position of the table, for example, can be displayed in the long image. Consequently, it is not necessary for the user to adjust the shape or size of the frame displayed in the long image. In addition, the user can adjust the imager or the table so as to obtain a desired imaging range while checking the frame in the long image.

In the aforementioned X-ray imaging apparatus according to this aspect, the image display preferably includes a plurality of image displays, and the X-ray image or the processed image and the long image are preferably displayed on the plurality of image displays different from each other. According to this structure, the long image and the X-ray image or the processed image can be displayed larger than when the long image and the X-ray image or the processed image are displayed on the same screen, and thus the accurate position and shape of the target portion can be more clearly grasped.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 1A is a side view showing the overall structure of an X-ray imaging apparatus according to first to third embodiments of the present invention.

FIG. 1B is a front view showing the overall structure of the X-ray imaging apparatus according to the first to third embodiments of the present invention.

FIG. 2 is a block diagram showing the overall structure of the X-ray imaging apparatus.

FIG. 3A is a diagram illustrating table movement imaging.

FIG. 3B is a diagram showing an example in which a plurality of positions are radiographed.

FIG. 4 is a diagram illustrating generation of a long image.

FIG. 5 is a side view illustrating the movement of the relative position of a table to an imager in the X-ray imaging apparatus according to the first embodiment.

FIG. 10A is a diagram illustrating a state before a change in the position of an imager according to the second embodiment.

FIG. 10B is a diagram illustrating a state after a change in the position of the imager according to the second embodiment.

FIG. 11A is a side view illustrating a state before a change in the height position of the table in the X-ray imaging apparatus according to the second embodiment.

FIG. 11B is a side view illustrating a state after a change in the height position of the table in the X-ray imaging apparatus according to the second embodiment.

FIG. 12A is a diagram illustrating a state before a change in the angle of the imager in the X-ray imaging apparatus according to the second embodiment.

FIG. 12B is a diagram illustrating a state after a change in the angle of the imager in the X-ray imaging apparatus according to the second embodiment.

DESCRIPTION OF THE PREFERRED EMBODIMENTS

Figure 6A:
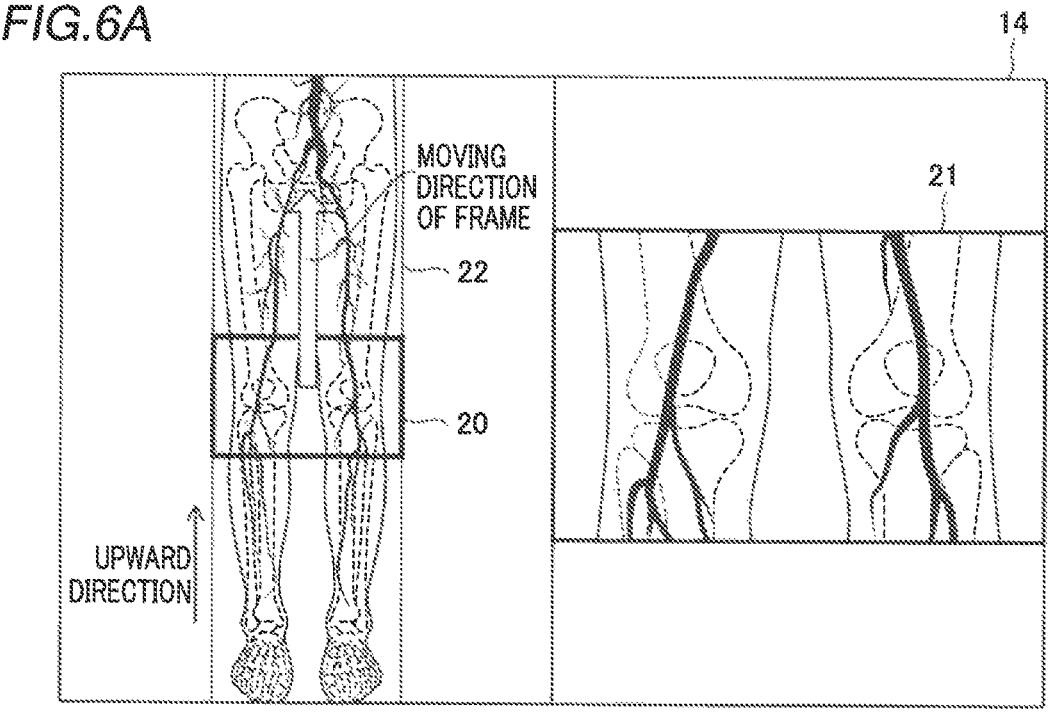
FIG. 6A is a diagram illustrating the long image and an X-ray image displayed on an image display in the X-ray imaging apparatus according to the first embodiment.

Embodiments of the present invention are hereinafter described with reference to the drawings.

First Embodiment

The structure of an X-ray imaging apparatus 100 according to a first embodiment of the present invention is now described with reference to FIGS. 1 to 7.

Structure of X-Ray Imaging Apparatus

As shown in FIG. 1A, the X-ray imaging apparatus 100 according to the first embodiment includes a table 1 on which a subject P is placed and an imager 2 including an X-ray tube device 3 and an X-ray receptor 4.

The table 1 has a rectangular flat plate shape in a plan view. The subject P is placed on the table 1 such that the head-foot direction of the subject P is along the long side of the rectangle, and the right-left direction of the subject P is along the short side of the rectangle. In this specification, the head-foot direction of the subject P is defined as a direction X, the right-left direction of the subject P is defined as a direction Y, and a direction orthogonal to the direction X and the direction Y is defined as a direction Z.

The X-ray tube device 3 includes an X-ray source and is disposed on a first side of the table 1. An X-ray tube drive (not shown) applies a voltage to the X-ray tube device 3 such that the X-ray tube device 3 can radiate X-rays. The X-ray tube device 3 includes a collimator 7 capable of adjusting an X-ray field, which is an X-ray irradiation range. Furthermore, as shown in FIG. 1B, the X-ray tube device 3 is attached to the tip of a first side of a C-shaped arm 6.

The X-ray receptor 4 is attached to the tip of a second side (the side opposite to the X-ray tube device 3) of the arm 6. That is, the X-ray receptor 4 can be disposed on a second side (the side opposite to the X-ray tube device 3) of the table 1 with the table 1 interposed between the X-ray receptor 4 and the X-ray tube device 3. In addition, the X-ray receptor 4 includes an FPD (flat panel detector) and can detect X-rays. Thus, the X-ray imaging apparatus 100 radiates X-rays by the X-ray tube device 3 in a state in which the subject P is placed on the table 1 and detects the X-rays transmitted through the subject P by the X-ray receptor 4 so as to capture X-ray images 21 (see FIG. 4). In addition, the X-ray receptor 4 is slidable in a direction (the direction Z in FIG. 1) in which a slider 8 extends by the slider 8 attached to the tip of the arm 6.

As shown in FIG. 2, the X-ray imaging apparatus 100 further includes a movement mechanism 9, a controller 10, an image display 14, a storage 15, and an operation unit 16.

The movement mechanism 9 can move the table 1 and the imager 2 in an arbitrary direction. That is, one or both of the table 1 and the imager 2 are moved in any one of the direction X, the direction Y, and the direction Z to change the relative positions of the table 1 and the imager 2 such that a position (imaging position; see FIG. 5) at which the subject P is imaged can be changed. Furthermore, the movement mechanism 9 can rotate the table 1 and the arm 6 (and eventually, the imager 2) on a plane (XZ plane) in the direction X and the direction Z and on a plane (YZ plane) in the direction Y and the direction Z. As described below, an angle between the table 1 and the imager 2 can be changed. Moreover, the movement mechanism 9 can slide the slider 8.

The controller 10 is a computer including a CPU (Central Processing Unit), a ROM (Read Only Memory), a RAM (Random Access Memory), etc. The controller 10 includes an image information acquirer 11, a position information acquirer 12, and an image processor 13.

The image information acquirer 11 acquires image information captured by the imager 2 from the X-ray receptor 4. The image information acquired by the image information acquirer 11 is stored in the storage 15, and the image processor 13 generates the X-ray images 21 with the image information.

The position information acquirer 12 acquires the position information of the table 1 and the imager 2 moved by the movement mechanism 9. As the position information of each of the table 1 and the imager 2, the coordinate information (X, Y, Z) of a plurality of positions is used. The position information of the imager 2 includes the position information of the X-ray tube device 3 and the X-ray receptor 4. For example, as the position information of the table 1, coordinate information (X, Y, Z) at positions near the four corners of the table 1 is used. As the position information of the imager 2, coordinate information (X, Y, Z) at four positions in total of any position of the X-ray tube device 3, any position of the X-ray receptor 4, and any two positions of the arm 6 is used, for example. As described above, the coordinate information of a plurality of positions of the table 1 and the imager 2 is used as the position information of the table 1 and the imager 2 such that the positions of the table 1 and the imager 2 can be specified even when one or both of the table 1 and the imager 2 move in one direction. Thus, even when the angle between the table 1 and the imager 2 is changed, for example, the position information aquifer 12 can treat the coordinate information of the plurality of positions as the position information of the table 1 and the imager 2.

The image processor 13 can generate the X-ray images 21 based on the image information acquired by the image information acquirer 11. The image processor 13 joins the X-ray images 21 captured by the imager 2 based on the position information of the table 1 and the imager 2 acquired by the position information acquirer 12 to generate a long image 22 (see FIG. 4).

The image display 14 is a liquid crystal display, for example. The image display 14 can display the X-ray images 21 generated by the image processor 13 based on the image information captured by the imager 2, and the long image 22 generated by joining a plurality of X-ray images 21 in the image processor 13.

The storage 15 includes a nonvolatile memory, for example. The storage 15 stores programs with which the move mechanism 9 and the image processor 13 perform processing, and can store the image information captured by the imager 2 and the position information of the table 1 and the imager 2 acquired by the position information acquirer 12 and the long image 22 generated by the image processor 13.

The operation unit 16 includes a mouse and a keyboard, for example. The operation unit 16 receives an input operation from a user. The operation unit 16 transmits the received input operation to the controller 10.

Method for Generating Long Image

A method for generating the long image 22 according to the first embodiment is now described with reference to FIGS. 3 and 4.

As shown in FIG. 3A, in the X-ray imaging apparatus 100 according to the first embodiment, a plurality of positions of the subject P can be radiographed while one or both of the table 1 and the imager 2 are moved by the movement mechanism 9. FIG. 3B shows an example in which a plurality of positions in the lower limb 30 of the subject P are radiographed.

Specifically, as shown in FIG. 3A, the table 1 is moved in the direction X and the direction Y with respect to the imager 2 such that X-ray imaging can be performed at a plurality of imaging positions, as shown in FIG. 3B. At this time, the image information acquirer 11 acquires the image information that has been acquired by X-ray imaging, and the position information acquirer 12 acquires the position information of the table 1 and the imager 2. In the following description, X-ray imaging at a plurality of imaging positions with the movement of the table 1 in the direction X and the direction Y with respect to the imager 2 may be referred to as "table movement imaging".

As shown in FIG. 4, the image processor 13 generates, from the image information acquired by X-ray imaging, the X-ray images 21 acquired by X-ray imaging at the plurality of imaging positions. According to the first embodiment, the table 1 is moved in the direction X such that imaging is performed from the abdomen to the toe of the subject P. The image processor 13 generates the long image 22 by joining the X-ray images 21 based on the position information of the table 1 and the imager 2 at the plurality of imaging positions.

As described above, the long image 22 generated by joining the X-ray images 21 is associated with the position information (imaging-time position information) of the table 1 and the imager 2 at the time of X-ray imaging to generate the X-ray images 21, and this information is stored in the storage 15.

Figure 6B:
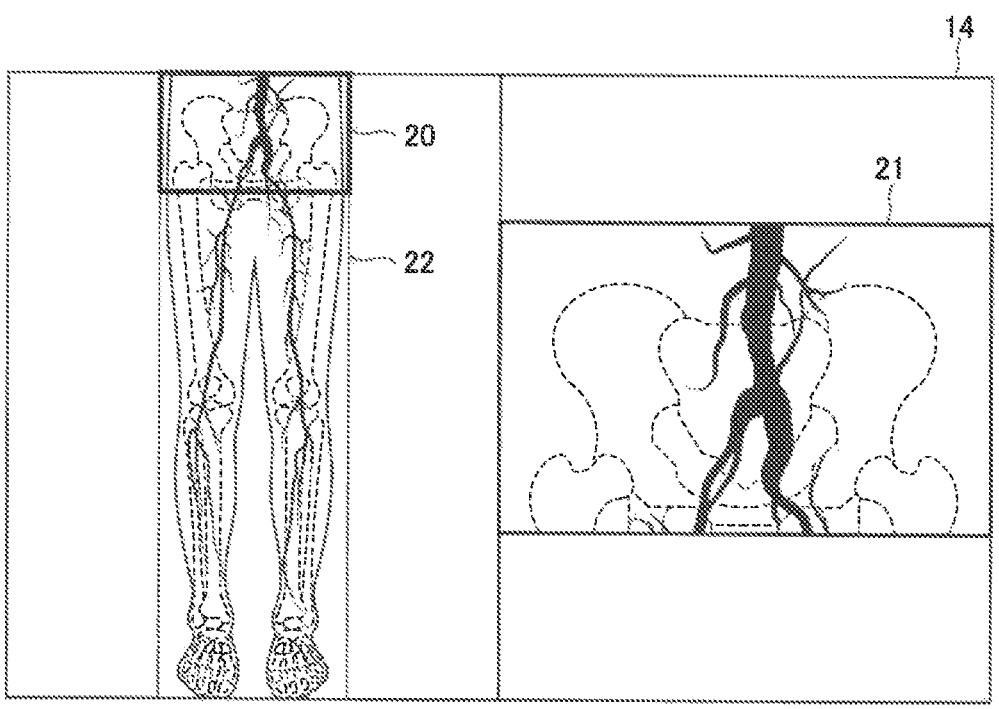
FIG. 6B is a diagram illustrating the long image and the X-ray image after the movement of the frame of the long image displayed on the image display in the X-ray imaging apparatus according to the first embodiment.

As shown in FIGS. 6A and 6B, in the X-ray imaging apparatus 100 according to the first embodiment, a frame 20 indicating the imaging range of the imager 2 can be superimposed and displayed on the long image 22. The frame 20 indicating this imaging range is a range in which X-rays radiated from the X-ray tube device 3 are detected in the X-ray receptor 4. That is, the frame 20 corresponds to a range generated as an X-ray image 21 when X-ray imaging or X-ray fluoroscopy is performed.

Specifically, the image processor 13 associates the imaging-time position information associated with the long image 22 with the position information of the table 1 and the imager 2, and superimposes and displays the frame 20 indicating the imaging range on the long image 22. At this time, the position information of the frame 20 becomes position information at a position at which the frame 20 is displayed, of the imaging-time position information associated with the long image 22. Furthermore, in a state in which the current imaging range of the imager 2 is indicated, the position information of the frame 20 corresponds to the coordinate information of the positions of the table 1 and the imager 2.

According to the first embodiment, as shown in FIGS. 6A and 6B, the image processor 13 displays the long image 22 in which the frame 20 indicating the imaging range of the imager 2 is displayed and the X-ray image 21 concurrently on the image display 14. Specifically, on the image display 14, the long image 22 and the X-ray image 21 are concurrently displayed side by side in the longitudinal direction (transverse direction in FIG. 6) of the image display 14.

Note that the X-ray image 21 displayed on the image display 14 concurrently with the long image 22 is an image containing position information that overlaps at least with the position information of the frame 20 among the X-ray images 21 used to create the long image 22. That is, an X-ray image 21 containing position information that at least partially overlaps with the position information (imaging-time position information) of the frame 20 currently displayed in the long image 22 is selected from among the X-ray images 21 used to create the long image 22, and is displayed on the image display 14 concurrently with the long image 22.

When there are a plurality of X-ray images 21 containing the position information that overlap at least with the position information of the frame 20, the image processor 13 selects and displays one of the plurality of X-ray images 21 based on a predetermined condition. The predetermined condition includes the overlapping amount of the position information or the time, for example. For example, among the plurality of X-ray images 21, an X-ray image 21 containing position information that most overlaps with the position information of the frame 20 may be selected by the image processor 13, or among the plurality of X-ray images 21, the latest (most recently captured) X-ray image 21 may be selected by the image processor 13. When a contrast medium slowly flows, there is a possibility that imaging of the same portion is continued until blood vessels are filled with the contrast medium. Even among X-ray images 21 obtained by imaging the same portion in this manner, a more recently captured X-ray image 21 can more clearly show the blood vessels. Furthermore, the user can set a condition for selecting the X-ray image 21 in advance in the image processor 13.

According to the first embodiment, the image processor 13 sequentially changes the X-ray image 21 to be displayed concurrently with the long image 22 on the image display 14 based on the movement of the frame 20 displayed in the long image 22. Specifically, when the frame 20 is moved, the image processor 13 selects an X-ray image 21 containing position information that at least partially overlaps with the position information of a portion of the long image 22 in which the frame 20 is displayed after the movement, based on the position information of the portion of the long image 22 in which the frame 20 is displayed after the movement acquired by the position information acquirer 12. The image processor 13 newly and sequentially selects the X-ray image 21 based on the position information of the portion of the long image 22 in which the frame 20 is displayed after the movement as the frame 20 is moved such that the X-ray image 21 to be displayed on the image display 14 concurrently with the long image 22 is sequentially changed. Also in this case, when there are a plurality of X-ray images 21 containing position information that overlaps at least with the position information of the portion of the long image 22 in which the frame 20 is displayed after the movement, one of the plurality of X-ray images 21 is selected and displayed based on the predetermined condition by the image processor 13.

In the X-ray imaging apparatus 100 according to the first embodiment, the relative position of the table 1 to the imager 2 is changed based on the movement of the frame 20 indicating the imaging range and displayed in the long image 22. Specifically, when the user moves the frame 20 displayed in the long image 22 from a state shown in FIG. 6A to a state shown in FIG. 6B by moving the frame 20 upward using the operation unit 16, the image processor 13 controls the movement mechanism 9 to move either the table 1 or the imager 2 so as to change the relative position of the table 1 to the imager 2. At this time, the controller 10 controls the movement mechanism 9 to change the relative position of the table 1 such that the relative position of the table 1 corresponds to the position information of the portion of the long image 22 in which the frame 20 is displayed after the movement. Accordingly, the relative position of the table 1 to the imager 2 is automatically changed such that the state shown in FIG. 6A is automatically changed to the state shown in FIG. 6B.

In the X-ray imaging apparatus 100 according to the first embodiment, even when the position of the subject P relative to the table 1 changes and the long image 22 becomes unclear, the accurate position and shape of a target portion of the long image 22 can be grasped with reference to the X-ray image 21 displayed concurrently with the long image 22.

Movement of Table Due to Movement of Frame

Figure 7:
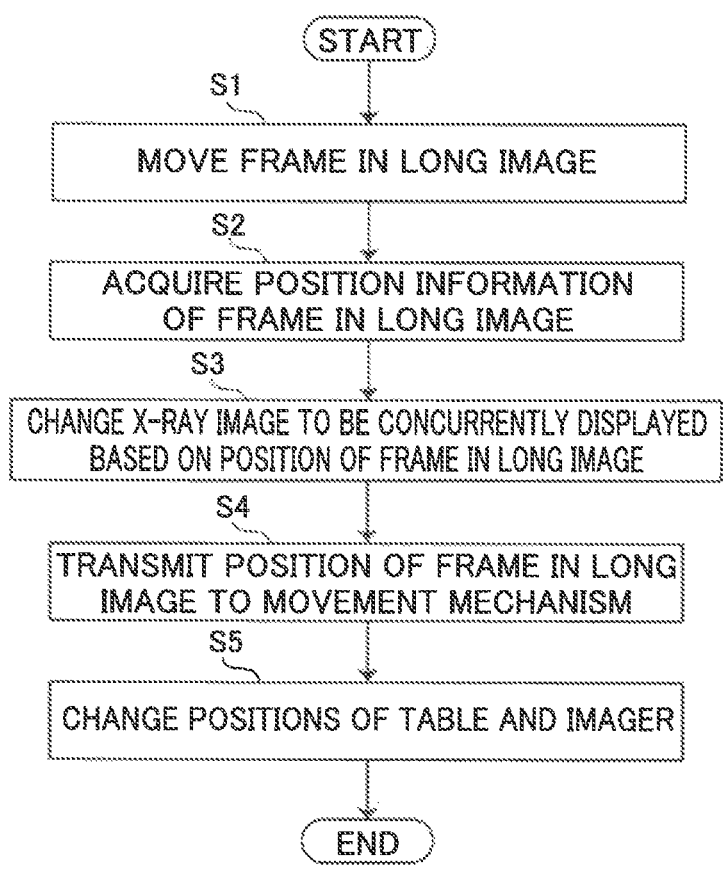
FIG. 7 is a diagram illustrating the operation procedure of the X-ray imaging apparatus according to the first embodiment.
Figure 8A:
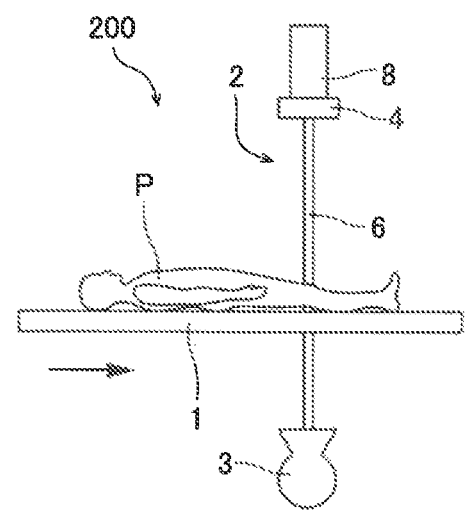
FIG. 8A is a side view illustrating a state before the movement of a table according to the second embodiment.
Figure 8B:
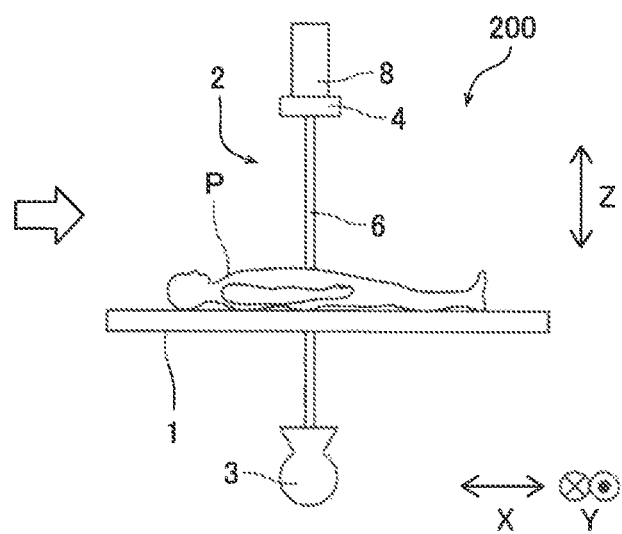
FIG. 8B is a side view illustrating a state after the movement of the table according to the second embodiment.

A control flow at the time of moving the frame 20 is now described with reference to FIG. 7. Before the frame 20 is moved, the position of the frame 20 displayed in the long image 22 corresponds to a current imaging position based on the current positions of the table 1 and the imager 2.

When the user performs an input operation on the frame 20 displayed in the long image 22 using the operation unit 16, the image processor 13 moves the frame 20 in the long image 22 according to the user's operation in step S1.

Then, in step S2, the position information acquirer 12 acquires the imaging-time position information associated with the portion of the long image 22 in which the frame 20 is displayed after the movement as the position information of the frame 20.

Then, in step S3, the image processor 13 selects the X-ray image 21 containing the position information that overlaps at least with the position information of the portion of the long image 22 in which the frame 20, which is currently displayed on the image display 14, is displayed, and changes the X-ray image 21 to be displayed concurrently with the long image 22 on the image display 14.

Then, in step S4, the position information acquirer 12 transmits the position information of the portion of the long image 22 in which the frame 20, which has been moved and is currently displayed on the image display 14, is displayed to the movement mechanism 9.

Then, in step S5, the controller 10 controls the movement mechanism 9 to change the relative position of the table 1 to the imager 2 to the same position as the position of the portion of the long image 22 in which the frame 20 is displayed based on the received position information of the frame 20 after the movement. Then, this control is terminated (see FIG. 7).

Advantageous Effects of First Embodiment

According to the first embodiment, the following advantageous effects are achieved.

According to the first embodiment, as described above, the X-ray imaging apparatus 100 concurrently displays, on the image display 14, the X-ray image 21 containing the position information that overlaps at least with the position information of the portion in which the frame 20 is displayed when displaying the frame 20 indicating the imaging range of the imager 2. Accordingly, misalignment that has occurred in the long image 22 can be compensated by visually checking the X-ray image 21 concurrently displayed on the image display 14, and thus the accurate position and shape of the target portion can be grasped. Furthermore, the X-ray image 21 that enables the user to accurately grasp the target portion is displayed on the image display 14, and the frame 20 indicating the imaging range of the imager 2 is displayed in the long image 22 such that the user can accurately grasp a portion to be imaged without performing additional X-ray irradiation to the subject P.

According to the first embodiment, in the X-ray imaging apparatus 100, the image processor 13 sequentially changes the X-ray image 21 to be displayed concurrently with the long image 22 on the image display 14, based on the movement of the frame 20 displayed in the long image 22. Accordingly, the X-ray image 21 to be displayed concurrently with the long image 22 is sequentially switched based on the movement of the frame 20 displayed in the long image 22, and thus the user can continue to grasp the accurate position and shape of each target portion according to the movement of the frame 20.

According to the first embodiment, the position information acquirer 12 acquires the position information of the portion of the long image 22 in which the frame 20 is displayed after the movement, and the image processor 13 sequentially changes the X-ray image 21 to be displayed concurrently with the long image 22 on the image display 14, based on the position information of the portion of the long image 22 in which the frame 20 is displayed after the movement acquired by the position information acquirer 12. Accordingly, when the frame 20 is moved, the X-ray image 21 containing the position information that overlaps at least with the position information of the portion of the long image 22 in which the frame 20 is displayed after the movement is constantly displayed on the image display 14 based on the position information of the portion of the long image 22 in which the frame 20 is displayed after the movement. Consequently, the X-ray image 21 containing the position information corresponding to the frame 20 displayed in the long image 22 can be more accurately and reliably displayed on the image display 14.

According to the first embodiment, the image processor 13 sequentially changes the X-ray image 21 to be displayed concurrently with the long image 22 on the image display 14, based on the position information of the portion of the long image 22 in which the frame 20 is displayed after the movement and the predetermined condition. Accordingly, the X-ray image 21 in accordance with the predetermined condition in addition to the position information can be displayed. Consequently, a more preferable X-ray image 21 used for treatment or diagnosis can be displayed on the image display 14 by appropriate setting of a condition such as setting, by the user, of a condition for selecting an image that enables the user to grasp the accurate position and shape of the target portion from among the plurality of X-ray images 21 obtained by imaging the same portion.

According to the first embodiment, the movement mechanism 9 changes the relative position of the table 1 to the imager 2 based on the movement of the frame 20 displayed in the long image 22 by the user's operation. Accordingly, when the frame 20 is moved by the user's operation, the relative position of the table 1 to the imager 2 is automatically changed, and thus the user does not need to move the table 1 and can more easily perform a step from treatment or diagnosis to imaging for the next treatment or diagnosis. In addition, when the frame 20 is moved by the user's operation, the relative position of the table 1 to the imager 2 is automatically changed, and thus the imager 2 can be moved to the target portion without additional X-ray irradiation.

Second Embodiment

A second embodiment is now described with reference to FIGS. 1, 2, and 8 to 14. This second embodiment differs from the first embodiment in that the position of a frame 223 displayed in a long image 22 is changed simultaneously with a change in the relative position of a table 1 to an imager 2 by a movement mechanism 9. In the figures, the same structures as those of the aforementioned first embodiment are denoted by the same reference numerals.

Figure 9A:
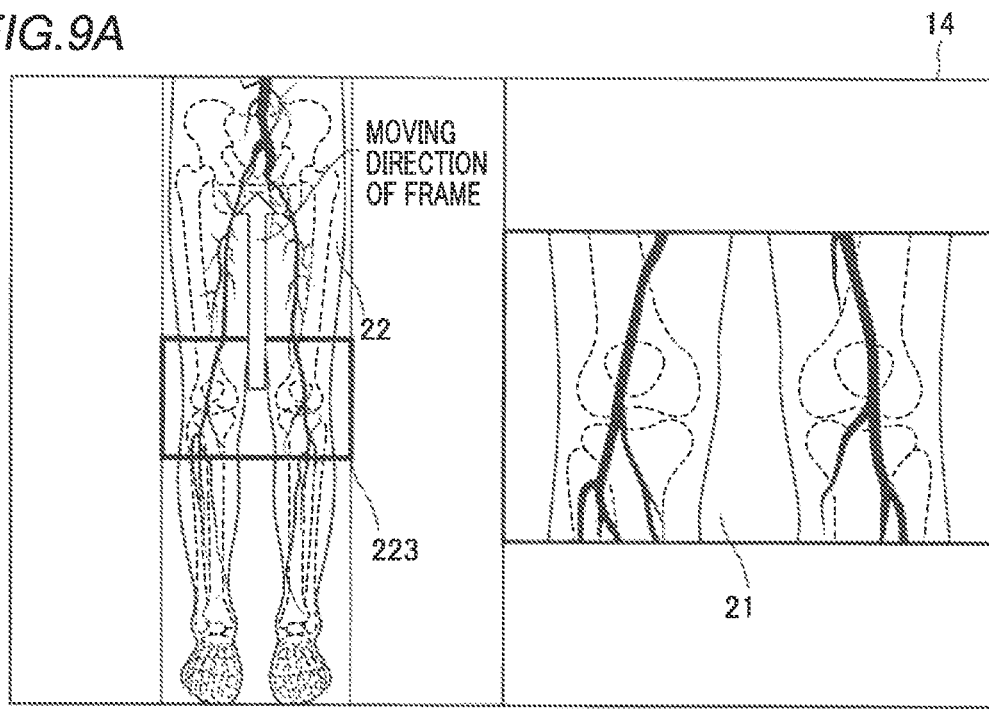
FIG. 9A is a diagram illustrating the movement of a frame displayed in a long image due to the movement of the table according to the second embodiment.
Figure 9B:
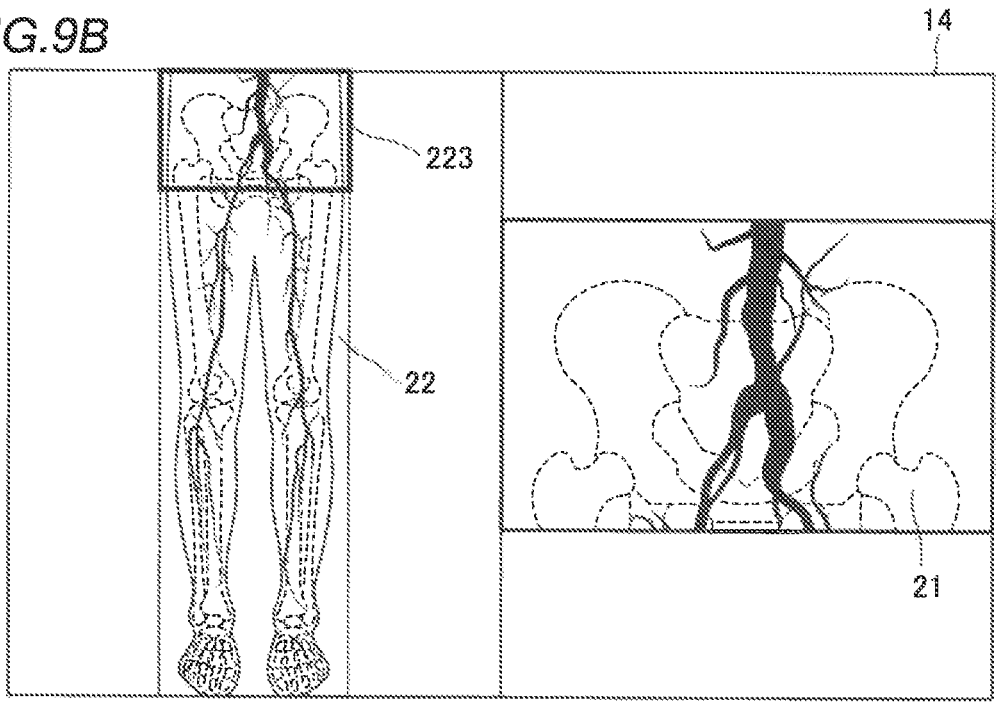
FIG. 9B is a diagram illustrating a state in which the frame displayed in the long image has moved due to the movement of the table according to the second embodiment.

In an X-ray imaging apparatus 200 (see FIGS. 1 and 2) according to the second embodiment of the present invention, the frame 223 indicates the current imaging range of the imager 2 based on the position information. The position of the frame 223 displayed in the long image 22 is moved based on the change in the relative position of the table 1 to the imager 2 by the movement mechanism 9. Specifically, when the relative position of the table 1 to the imager 2 is changed such that the table 1 is moved by the movement mechanism 9 from a state shown in FIG. 8A to a state shown in FIG. 8B, an image processor 213 moves the display position of the frame 223 displayed in the long image 22 such that a state shown in FIG. 9A is changed to a state shown in FIG. 9B based on the position information of the table 1 and the imager 2.

In the X-ray imaging apparatus 200 according to the second embodiment, a distance between an X-ray tube device 3 and an X-ray receptor 4 is changed such that the size of the frame 223 displayed in the long image 22 is changed.

Specifically, in the X-ray imaging apparatus 200, when the movement mechanism 9 slides a slider 8 based on an external instruction or a user's manual operation in a state in which the current frame 223 is displayed in the long image 22 so as to change the distance between the X-ray tube device 3 and the X-ray receptor 4, as shown in FIG. 10, a position information acquirer 12 acquires the position information of the X-ray tube device 3 and the X-ray receptor 4 before and after the change in the distance between the X-ray tube device 3 and the X-ray receptor 4. As shown in FIG. 10, the image processor 213 adjusts the size of the current frame 223 in the long image 22 based on the position information acquired by the position information acquirer 12. The distance between the X-ray tube device 3 and the X-ray receptor 4 is changed in this manner such that the frame 223 displayed on the long image 22 can be enlarged or reduced.

FIG. 10 shows the case in which the distance between the X-ray tube device 3 and the X-ray receptor 4 is increased by changing from the state shown in FIG. 10A to the state shown in FIG. 10B. In this case, the center position of the frame 223 displayed in the long image 22 does not change, and the range thereof becomes small. When the distance between the X-ray tube device 3 and the X-ray receptor 4 is reduced, the center position of the frame 223 displayed in the long image 22 does not change, and the range thereof becomes large.

In the X-ray imaging apparatus 200 according to the second embodiment, the height position of the table 1 is changed such that the size of the frame 223 displayed in the long image 22 is changed.

Specifically, the movement mechanism 9 raises and lowers the table 1 in a state in which the current frame 223 is displayed in the long image 22 so as to change the height position of the table 1, as shown in FIG. 11. The position information acquirer 12 acquires the position information of the table 1 before and after the change in the height position of the table 1. The image processor 213 adjusts the size of the current frame 223 in the long image 22 based on the position information acquired by the position information acquirer 12. The height position of the table 1 is changed in this manner such that the frame 223 displayed in the long image 22 can be easily enlarged or reduced. FIG. 11 shows the case in which the table 1 is lowered and is moved away from the X-ray receptor 4 by changing from a state shown in FIG. 11A to a state shown in FIG. 11B. In this case, the center position of the frame 223 displayed in the long image 22 does not change, and the range thereof becomes small. When the table 1 is raised and is moved closer to the X-ray receptor 4, the center position of the frame 223 displayed in the long image 22 does not change, and the range thereof becomes large.

In the X-ray imaging apparatus 200 according to the second embodiment, an angle between the table 1 and the imager 2 is changed such that the shape of the frame 223 displayed in the long image 22 is changed.

Specifically, the movement mechanism 9 rotates an arm 6 on a plane (XZ plane) in a direction X and a direction Z in a state in which the current frame 223 is displayed in the long image 22 so as to change the angle between the table 1 and the imager 2, as shown in FIG. 12A. The position information acquirer 12 acquires the position information of the table 1 and the imager 2 before and after the change in the angle between the table 1 and the imager 2. As shown in FIG. 12B, the image processor 213 adjusts the shape of the current frame 223 in the long image 22 based on the position information acquired by the position information acquirer 12. In FIG. 12, the X-ray irradiation direction with respect to the table 1 is inclined in the XZ plane such that the current frame 223 in the long image 22 has a rectangular shape longer in the direction X. The angle between the table 1 and the imager 2 is changed in this manner such that frames 223 corresponding to various angles can be displayed in the long image 22.

In the X-ray imaging apparatus 200 according to the second embodiment, the angle between the table 1 and the imager 2 is changed such that the shape of the frame 223 displayed in the long image 22 is changed.

Figure 13:
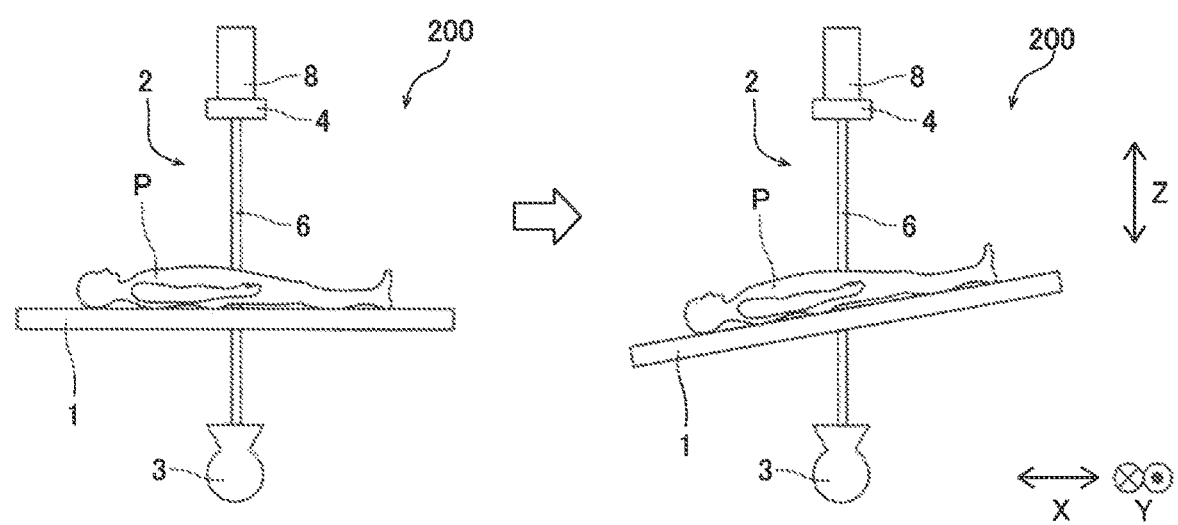
FIG. 13 is a side view illustrating a change in the angle of the table in the X-ray imaging apparatus according to the second embodiment.
Figure 14:
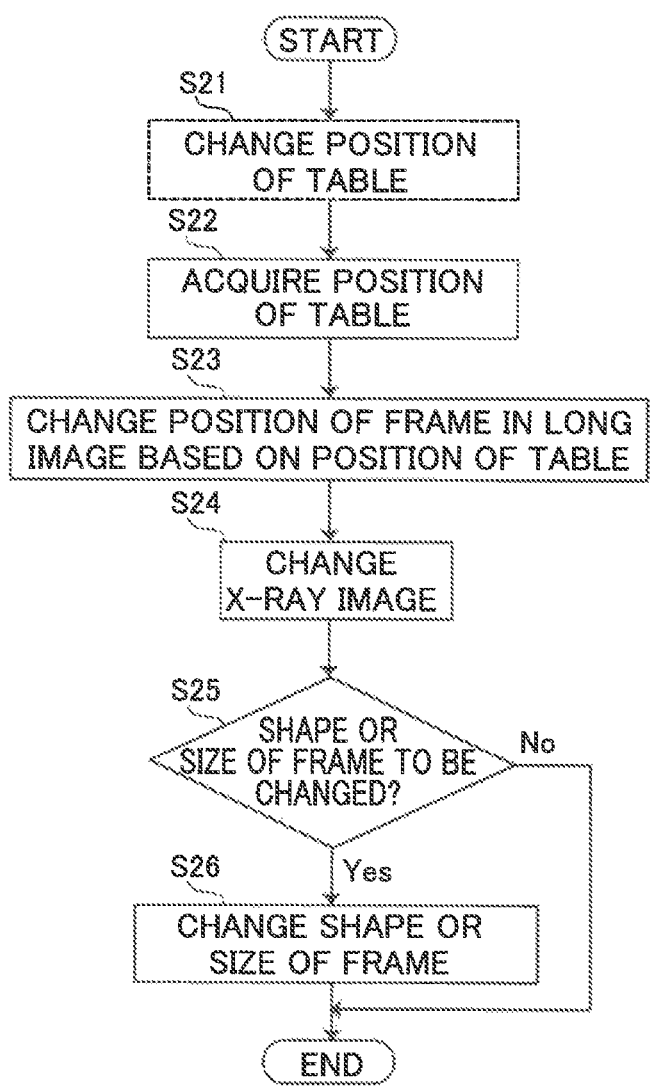
FIG. 14 is a diagram illustrating the operation procedure of the X-ray imaging apparatus according to the second embodiment.

Specifically, the movement mechanism 9 rotates the table 1 on the plane (XZ plane) in the direction X and the direction Z in a state in which the current frame 223 is displayed in the long image 22 so as to change the angle between the table 1 and the imager 2, as shown in FIG. 13. The position information acquirer 12 acquires the position information of the table 1 and the imager 2 before and after the change in the angle between the table 1 and the imager 2. The image processor 213 adjusts the shape of the current frame 223 in the long image 22, as shown in FIG. 12, based on the position information acquired by the position information acquirer 12. The angle between the table 1 and the imager 2 is changed in this manner such that frames 223 corresponding to various angles can be displayed in the long image 22.

In the X-ray imaging apparatus 200 according to the second embodiment, the X-ray field of the X-ray tube device 3 is changed such that the size of the frame 223 displayed in the long image 22 is changed.

Specifically, in a state in which the current frame 223 is displayed in the long image 22, a collimator 7 is controlled to change the X-ray field of the X-ray tube device 3. The image processor 213 adjusts the size of the current frame 223 in the long image 22 based on control information for controlling the collimator 7. For example, when the collimator 7 reduces the X-ray field, the frame 223 that has been enlarged is displayed in the long image 22 based on the long image 22 and the position information of the frame 223 in the long image 22. When the collimator 7 enlarges the X-ray field, the frame 223 that has been reduced is displayed in the long image 22. The X-ray field of the X-ray tube device 3 is changed in this manner such that the frame 223 displayed in the long image 22 can be easily enlarged or reduced.

The remaining structures of the X-ray imaging apparatus 200 according to the second embodiment are similar to those of the aforementioned first embodiment. The case in which the frame 223 displayed in the long image 22 is changed due to the movement of the table 1 according to the second embodiment of the present invention is now described with reference to FIG. 14.

In step S21, the relative position of the table 1 to the imager 2 is moved, as shown in FIG. 8. Note that a controller 10 may automatically perform the processing in step S21 based on an external instruction, for example, or the user may manually move the table 1.

Then, in step S22, the position information acquirer 12 acquires the current position information of the table 1 and the imager 2.

Then, in step S23, the image processor 213 moves the frame 223 displayed in the long image 22 based on the position information of the table 1 and the imager 2. The image processor 213 associates imaging-time position information associated with the long image 22 with the current position information of the table 1 and the imager 2, and displays the frame 223, which is displayed in the long image 22, as an imaging position based on the current positions of the table 1 and the imager 2 on an image display 14. Accordingly, as shown in FIG. 9, the current frame 223 displayed in the long image 22 moves by an amount corresponding to the change in the relative position of the table 1 to the imager 2.

Then, in step S24, the image processor 213 selects an X-ray image 21 containing position information that overlaps at least with the position information of the frame 223, and changes an X-ray image 21 to be displayed concurrently with the long image 22 on the image display 14. Then, in step S25, the image processor 213 determines whether or not to change the shape or size of the frame 223 due to a change in the distance between the X-ray tube device 3 and the X-ray receptor 4, for example. When determining to change the shape or size of the frame 223, the image processor 213 changes the shape or size of the frame 223 as appropriate in step S26. Then, this control is terminated. When determining not to change the shape or size of the frame 223 in step S25, this control is terminated.

Advantageous Effects of Second Embodiment

According to the second embodiment, the following advantageous effects are achieved.

According to the second embodiment, the frame 223 indicates the current imaging range of the imager 2 based on the position information, and the image processor 213 moves the frame 223 displayed in the long image 22 based on the change in the relative position of the table 1 to the imager 2 by the movement mechanism 9. Accordingly, the frame 223 displayed in the long image 22 is automatically moved to a portion corresponding to the imaging range of the imager 2 after the change simultaneously with the change in the relative position of the table 1 to the imager 2, and thus it is not necessary for the user to perform an operation of moving the frame 223 in the long image 22. In addition, when changing the relative positions of the imager 2 and the table 1 so as to obtain a desired imaging position, the user can perform it while checking the frame 223 in the long image 22 and the X-ray image 21, and thus positioning can be performed more easily.

According to the second embodiment, the image processor 213 adjusts the shape or size of the frame 223 displayed in the long image 22 based on the change in the position information due to the change in the position of the imager 2, the change in the position information due to the change in the height position of the table 1, the change in the position information due to the change in the angle between the table 1 and the imager 2, or the change in the X-ray field of the imager 2. Accordingly, the frame 223 that reflects the change in the height position of the table 1, for example, can be displayed in the long image 22. Consequently, it is not necessary for the user to adjust the shape or size of the frame 223 displayed in the long image 22. In addition, the user can adjust the imager 2 or the table 1 so as to obtain a desired imaging range while checking the frame 223 in the long image 22. The remaining advantageous effects of the second embodiment are similar to those of the aforementioned first embodiment.

Third Embodiment

A third embodiment is now described with reference to FIGS. 1, 2, 15, and 16. This third embodiment differs from the first embodiment and the second embodiment in that an X-ray imaging apparatus 300 (see FIGS. 1 and 2) displays, on an image display 14, a processed image 21c acquired by performing image processing on an X-ray image 21, instead of the X-ray image 21. In the figures, the same structures as those of the aforementioned first embodiment are denoted by the same reference numerals.

Figure 15A:
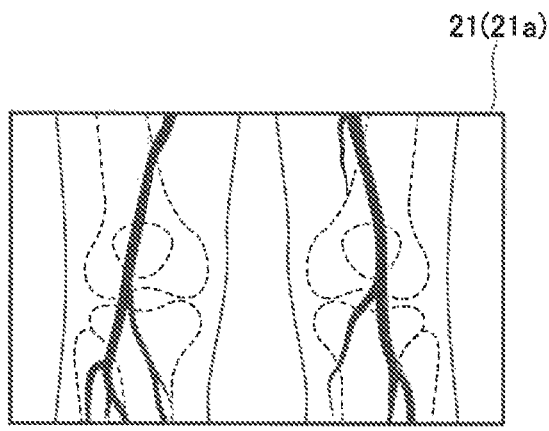
FIG. 15A is a diagram illustrating an X-ray image captured in a state in which a contrast medium is administered according to the third embodiment.

The processed image 21c is an image acquired by performing image processing in order to further clarify a target portion to be imaged, for example, based on the X-ray image 21. For example, when desiring to capture an X-ray image 21 of blood vessels, a user administers a contrast medium to a patient and captures the image. As shown in FIG. 15A, the acquired X-ray image 21 (21a) is captured with the bones that absorb X-rays.

Figure 15B:
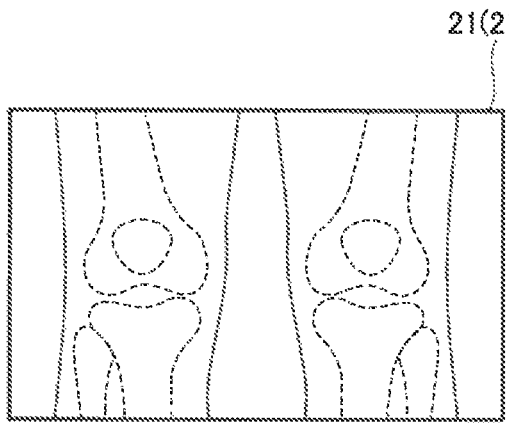
FIG. 15B is a diagram illustrating an X-ray image captured without administering the contrast medium according to the third embodiment.
Figure 15C:
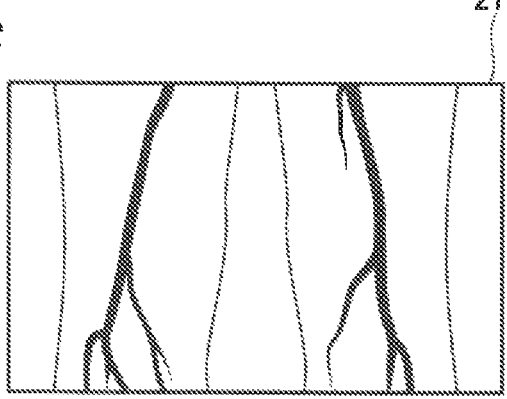
FIG. 15C is a diagram illustrating a processed image according to the third embodiment.

As shown in FIG. 15B, in an X-ray image 21 (21b) without the contrast medium acquired by imaging the same portion, only the bones are imaged without the blood vessels being imaged. Using the X-ray image 21 (21b) without the contrast medium being administered, image processing is performed such that bone portions are deleted from the X-ray image 21 (21a) with the administered contrast medium, as shown in FIG. 15C. Thus, the processed image 21c in which only the blood vessels are imaged can be acquired.

Figure 16:
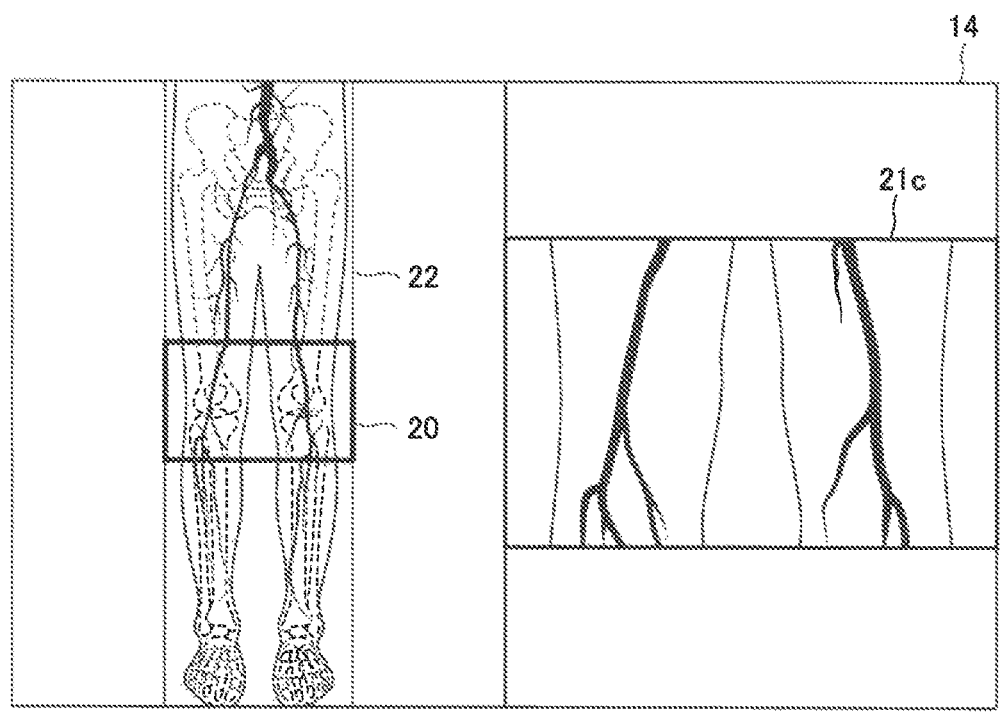
FIG. 16 is a diagram illustrating a long image and the processed image displayed on an image display in the X-ray imaging apparatus according to the third embodiment.

As shown in FIG. 16, an image processor 13 displays a long image 22 in which a frame 20 indicating the imaging range of an imager 2 is displayed and the processed image 21c containing position information that at least partially overlaps with the position information (imaging-time position information) of the frame 20 currently displayed in the long image 22 concurrently on the image display 14.

The remaining structures of the X-ray imaging apparatus 300 according to the third embodiment are similar to those of the aforementioned first and second embodiments.

Advantageous Effects of Third Embodiment

According to the third embodiment, when the frame 20 indicating the imaging range of the imager 2 is displayed, the processed image 21c containing the position information that overlaps at least with the position information of the frame 20 is concurrently displayed on the image display 14. Accordingly, similarly to the first embodiment, the accurate position and shape of a target portion can be grasped. Furthermore, the processed image 21c on which the image processing has been performed is displayed concurrently with the long image 22 on the image display 14 such that as compared with the case in which the X-ray image 21 on which the image processing has not yet been performed is displayed, the accurate position and shape of the target portion can be more reliably grasped. The remaining advantageous effects of the third embodiment are similar to those of the aforementioned first and second embodiments.

Modified Examples

The embodiments disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included.

For example, while the table movement imaging is performed by moving the table in the direction X and the direction Y with respect to the imager in each of the aforementioned first to third embodiments, the present invention is not restricted to this. According to the present invention, the table movement imaging may alternatively be performed by moving the imager in the direction X and the direction Y with respect to the table. Furthermore, the table and the imager may alternatively be moved only in one of the direction X and the direction Y. In addition, the table movement imaging may alternatively be performed by moving one of the table and the imager in the direction X or (and) the direction Y as well as in the direction Z.

While the controller includes the image information acquirer, the position information acquirer, and the image processor in each of the aforementioned first to third embodiments, the present invention is not restricted to this. According to the present invention, the image information acquirer, the position information acquirer, and the image processor may alternatively be provided separately from the controller.

While the coordinate information (X, Y, Z) is used as the position information of the table and the imager acquired by the position information acquirer in each of the aforementioned first to third embodiments, the present invention is not restricted to this. According to the present invention, not only a Cartesian coordinate system as in the coordinate information (X, Y, Z) but also another coordinate system such as a polar coordinate system may alternatively be used to acquire the position information of the table and the imager.

While when the imaging range is displayed in the long image, the movement mechanism rotates the arm on the plane (XZ plane) in the direction X and the direction Z to change the angle between the table and the imager in the aforementioned second embodiment, the present invention is not restricted to this. According to the present invention, when the imaging range is displayed in the long image, the movement mechanism may alternatively rotate the arm on the plane (YZ plane) in the direction Y and the direction Z to change the angle between the table and the imager.

While when the imaging range is displayed in the long image, the movement mechanism rotates the table on the plane (XZ plane) in the direction X and the direction Z to change the angle between the table and the imager in the aforementioned second embodiment, the present invention is not restricted to this. According to the present invention, when the imaging range is displayed in the long image, the movement mechanism may alternatively rotate the table on the plane (YZ plane) in the direction Y and the direction Z to change the angle between the table and the imager.

While the lower limb of the subject P is radiographed in each of the aforementioned first to third embodiments, the present invention is not restricted to this. According to the present invention, a portion other than the lower limb such as the arm or the trunk of the subject P may alternatively be radiographed. Furthermore, according to the present invention, the X-ray imaging apparatus may alternatively image not only a human body but also a subject such as an animal body other than a human body.

While the time or the overlapping amount of the position information is used as the condition for selecting an X-ray image in each of the aforementioned first to third embodiments, the present invention is not restricted to this. According to the present invention, the presence or absence of the contrast medium, the magnitude of a pixel value, etc. other than the overlapping amount of the position information or the time may alternatively be used as the condition to select an X-ray image to be displayed concurrently with the long image from among a plurality of X-ray images.

While each of the aforementioned first to third embodiments is described as an independent embodiment, the present invention is not restricted to this. According to the present invention, any ones of the aforementioned first to third embodiments may alternatively be combined.

Figure 17A:
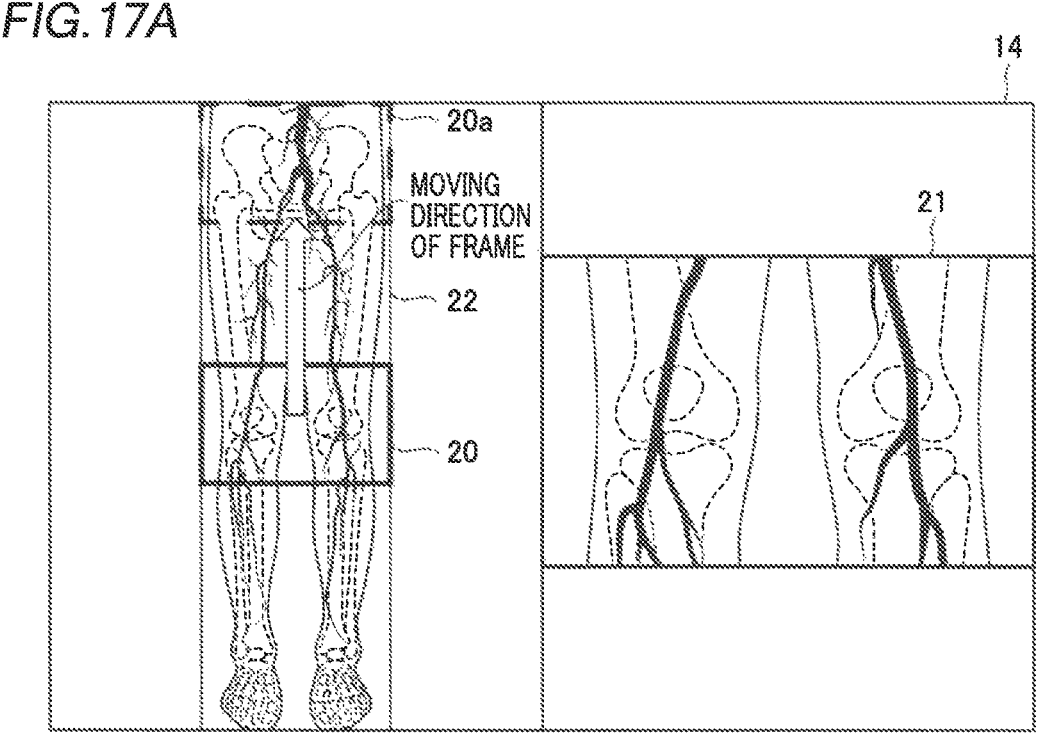
FIG. 17A is a diagram showing a modified example of the frame displayed in the long image before the movement of the table.
Figure 17B:
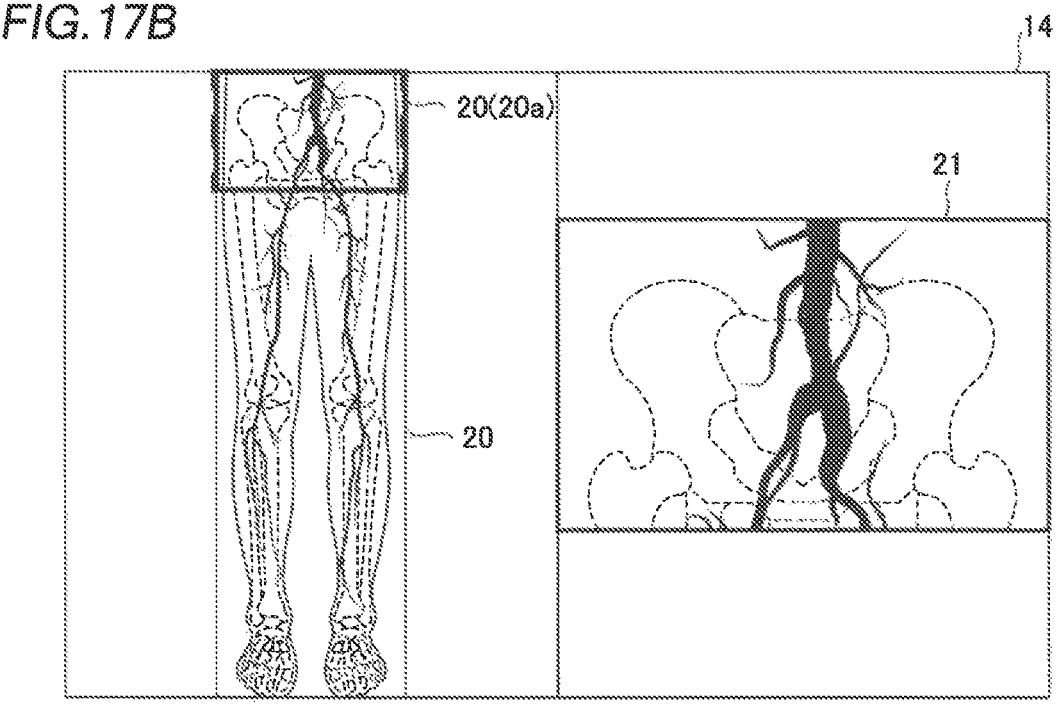
FIG. 17B is a diagram showing a modified example of the frame displayed in the long image after the movement of the table.

While the example in which one frame 20 is displayed in the long image 22 has been shown in FIG. 6 of the aforementioned first embodiment, the present invention is not restricted to this. For example, when the table is moved from a state shown in FIG. 17A, the frame 20 (solid line) indicating the current irradiation position and a frame 20a (broken line) indicating the movement destination of the table may alternatively be displayed in the long image 22, and the two frames 20 and 20a may alternatively be superimposed as shown in FIG. 17B upon completion of the movement of the table. In this case, the X-ray image 21 to be displayed concurrently with the long image 22 may be switched upon completion of the movement of the table, or the X-ray image 21 to be displayed concurrently with the long image 22 may be switched in accordance with the movement of the table before the completion of the movement of the table (during the movement of the table).

While the entire long image is displayed on the image display in each of the aforementioned first to third embodiments, the present invention is not restricted to this. According to the present invention, only a partial display range of the long image may alternatively be displayed on the image display, and the display range of the long image may alternatively be displayed as a moving image so as to change with the lapse of time. In this case, when the user selects the display range of the long image containing the target portion for diagnosis or treatment, the movement of the long image preferably stops, and the display range of the long image is preferably displayed as a still image on the image display.

While the X-ray imaging apparatus includes one image display in each of the aforementioned first to third embodiments, the present invention is not restricted to this. According to the present invention, the X-ray imaging apparatus may alternatively include a plurality of image displays. In this case, it is preferable to display the long image and the X-ray image or the processed image concurrently on different image displays. Thus, the long image and the X-ray image or the processed image can be displayed larger than when the long image and the X-ray image or the processed image are displayed on the same screen, and thus the accurate position and shape of the target portion can be more clearly grasped.

While the image processor sequentially changes the X-ray image to be displayed concurrently with the long image on the image display based on the movement of the frame displayed in the long image in the aforementioned first embodiment, the present invention is not restricted to this. According to the present invention, a decision button may alternatively be displayed on the image display to determine the position of the frame, and the X-ray image to be displayed concurrently with the long image on the image display may alternatively be changed when the user operates the decision button.

What is claimed is:

1. An X-ray imaging apparatus comprising:
a table on which a subject is placed;
an imager that irradiates the subject with X-rays, detects the X-rays transmitted through the subject, and captures a plurality of X-ray images;
a movement mechanism that changes a relative position of the table to the imager;
a position information acquirer that acquires position information about the relative position of the table to the imager;
an image processor that joins the plurality of X-ray images captured with a change in the relative position by the movement mechanism based on the position information acquired by the position information acquirer to generate a long image; and
an image display that displays an X-ray image of the plurality of X-ray images or a processed image obtained by performing image processing on the X-ray image and the long image, wherein
the image processor concurrently displays, on the image display, the long image in which a frame indicating an imaging range of the imager is displayed and the X-ray image or the processed image containing position information that overlaps at least with position information of a portion of the long image in which the frame is displayed;
and wherein the image processor selects an X-ray image containing position information that overlaps at least with the position information of the frame, and changes an X-ray image or the processed image to be displayed concurrently with the long image on the image display.

2. The X-ray imaging apparatus according to claim 1, wherein the image processor sequentially changes the X-ray image or the processed image to be displayed concurrently with the long image on the image display, based on movement of the frame displayed in the long image.

3. The X-ray imaging apparatus according to claim 2, wherein
the position information acquirer acquires the position information of the portion of the long image in which the frame is displayed after the movement, and
the image processor sequentially changes the X-ray image or the processed image to be displayed concurrently with the long image on the image display, based on the position information of the portion of the long image in which the frame is displayed after the movement acquired by the position information acquirer.

4. The X-ray imaging apparatus according to claim 3, wherein the image processor sequentially changes the X-ray image or the processed image to be displayed concurrently with the long image on the image display, based on the position information of the portion of the long image in which the frame is displayed after the movement and a predetermined condition.

5. The X-ray imaging apparatus according to claim 1, wherein the movement mechanism changes the relative position of the table to the imager based on movement of the frame displayed in the long image by a user's operation.

6. The X-ray imaging apparatus according to claim 1, wherein
the frame indicates a current imaging range of the imager based on the position information, and
the image processor moves the frame displayed in the long image based on the change in the relative position of the table to the imager by the movement mechanism.

7. The X-ray imaging apparatus according to claim 6, wherein the image processor adjusts a shape or size of the frame displayed in the long image based on a change in the position information due to a change in a position of the imager, the change in the position information due to a change in a height position of the table, the change in the position information due to a change in an angle between the table and the imager, or a change in an X-ray field of the imager.

8. The X-ray imaging apparatus according to claim 1, wherein the image display includes a plurality of image displays, and the X-ray image or the processed image and the long image are displayed on the plurality of image displays different from each other.

9. The X-ray imaging apparatus according to claim 1, wherein when there are a plurality of X-ray images that contain position information that overlap at least with the position information of the frame, the image processor selects and displays one of the plurality of X-ray images based on a predetermined condition.

10. The X-ray imaging apparatus according to claim 9, wherein the predetermined condition includes an overlapping amount of the position information or a time.

11. The X-ray imaging apparatus according to claim 10, wherein among the plurality of X-ray images, an X-ray image containing position information that most overlaps with the position information of the frame is selected by the image processor.

12. The X-ray imaging apparatus according to claim 10, wherein among the plurality of X-ray images, the most recently captured X-ray image is selected by the image processor.

13. The X-ray imaging apparatus according to claim 10, wherein when a position of the subject relative to the table changes and the long image becomes unclear, an accurate position and shape of a target portion of the long image can be grasped with reference to the X-ray image displayed concurrently with the long image.

14. The X-ray imaging apparatus according to claim 1, wherein the long image generated by joining the X-ray images is associated with the imaging-time position information of the table and the imager at the time of capturing the X-ray images, and wherein the imaging-time position information is stored in a storage.

15. The X-ray imaging apparatus according to claim 14, wherein the image processor associates the imaging-time position information associated with the long image with the position information of the table and the imager, and superimposes and displays the frame indicating the imaging range on the long image.

16. The X-ray imaging apparatus according to claim 15, wherein the position information of the frame corresponds to the coordinate information of positions of the table and the imager.

17. The X-ray imaging apparatus according to claim 14, wherein the storage includes a non-volatile memory.

18. The X-ray imaging apparatus according to claim 1, wherein the user moves the frame displayed in the long image.

19. The X-ray imaging apparatus according to claim 18, further comprising an operation unit to receive input operation from the user.

20. The X-ray imaging apparatus according to claim 19, wherein the operation unit includes a keyboard and mouse.

* * * * *